US00PP24509P3

(12) United States Plant Patent
Pavlich

(10) Patent No.: US PP24,509 P3
(45) Date of Patent: May 27, 2014

(54) *SALVIA* PLANT NAMED 'SILVER SABRE'

(50) Latin Name: *Salvia officinalis*
Varietal Denomination: Silver Sabre

(76) Inventor: John C. Pavlich, East Olympia, WA (US)

( * ) Notice: Subject to any disclaimer, the term of this patent is extended or adjusted under 35 U.S.C. 154(b) by 386 days.

(21) Appl. No.: 13/200,434

(22) Filed: Sep. 22, 2011

(65) Prior Publication Data

US 2013/0081186 P1 Mar. 28, 2013

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Klarquist Sparkman, LLP

(57) ABSTRACT

A new and distinct form of *Salvia* plant characterized an evenly white, variegated margin, a low, well-branched habit, and excellent vigor.

1 Drawing Sheet

Botanical denomination: *Salvia officinalis*.
Variety designation: 'Silver Sabre'.

BACKGROUND OF THE INVENTION

The present invention relates to a new and distinct cultivar of *Salvia,* given the name, 'Silver Sabre'. *Salvia* is in the family Lamiaceae. This new cultivar was found as a branch mutation of *Salvia officinalis* 'Tricolor' (unpatented). Compared to *Salvia officinalis* 'Tricolor' the new cultivar has a lower, more branched habit due to compressed internodes, and more evenly white marginal variegation. The new cultivar exhibits the pink new growth of the parent plant.

SUMMARY OF THE INVENTION

This plant exhibits the following characteristics that make it unique:

1. an evenly white, variegated margin,
2. a low well-branched habit, and
3. excellent vigor.

The new variety has been reproduced only by asexual propagation (stem cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
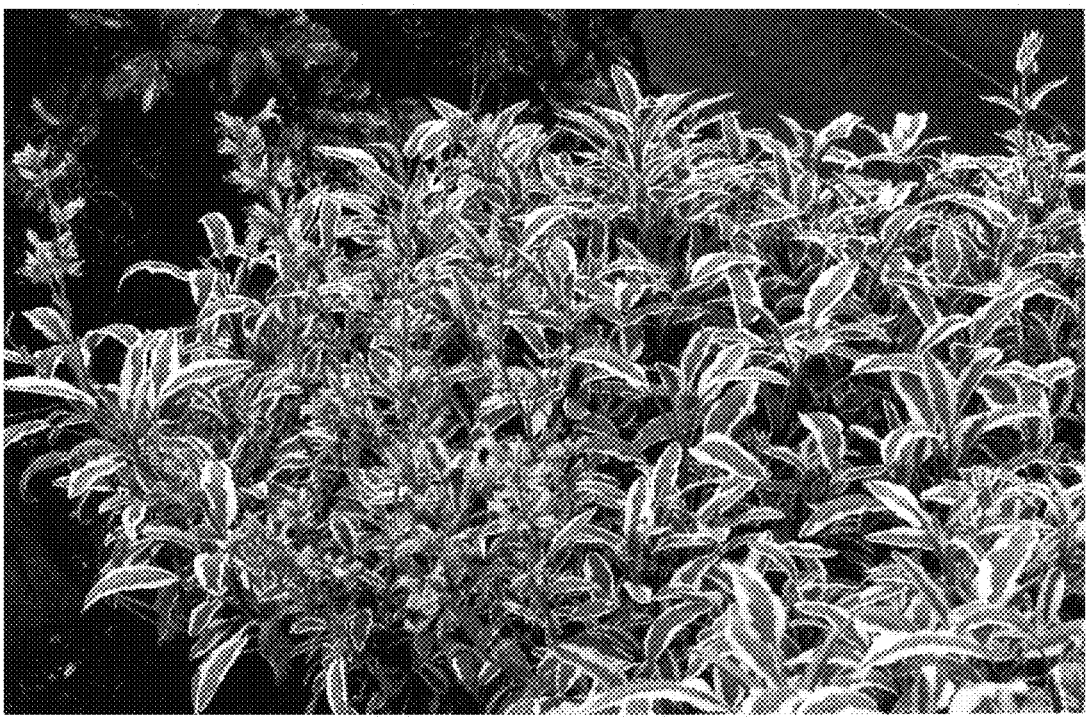
FIG. 1 shows a one-year-old *Salvia* 'Silver Sabre' growing in the trial field in late June in Canby, Oreg.
Figure 2:
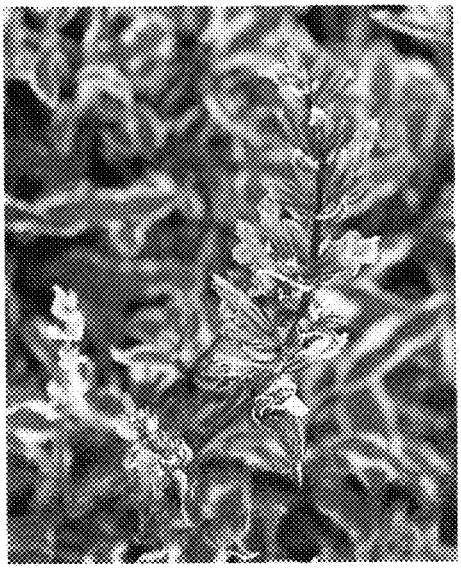
FIG. 2 shows a close up of the flower.

The following is a detailed description of the new *Salvia* cultivar based on observations of one-year-old specimens in late June grown outside in the ground in the trial beds in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Form.*—Upright.
*Type.*—Perennial to subshrub.
*Cold hardiness.*—USDA Zone 5-8.
*Size.*—Grows to 58 cm wide and 21 cm tall to the top of the foliage.
*Vigor.*—Excellent.
*Branching.*—Numerous, tight branching system.
*Number of leaves per stem.*—15 on average.
*Stem.*—Square in cross section, where herbaceous and non flowering it grows to 17 mm long unbranched, pubescent, internodes range from 5 to 30 mm long, Greyed Purple N186C; older woody stems grow to 7 mm wide, Brown 200A.
*Roots.*—Fibrous, plants root easily from stem tip cuttings.

Leaf:

*Type.*—Simple.
*Arrangement.*—Opposite.
*Blade size.*—About 42 mm long and 12 mm wide.
*Petiole description.*—38 mm long and 1 mm wide, Yellow Green 147B except very base where Greyed Purple 187A.
*Shape.*—Lanceolate.
*Venation.*—Pinnate.
*Margins.*—Irregularly crenulate.
*Apex.*—Acute.
*Base.*—Cuneate.
*Surface texture.*—Pubescent of both sides, rugose.
*Leaf color.*—Top side Yellow Green 147A with margins White 155A, bottom side Yellow Green 147B with margins White 155A; new leaves tinted Greyed Purple 186C on top and bottom sides, showing most prominently near green centers as leaves expand.

Inflorescence:

*Type.*—Terminal raceme with verticillasters in 4 to 8 whorls.

*Number of flowers.*—10 to 30 per raceme.

*Size of inflorescence.*—Grows to 22 cm tall and 7 cm wide.

*Peduncle.*—Grows to 20 cm tall and 3 mm wide, pubescent, Yellow Green 146C tinted Greyed Purple N186C.

*Pedicel.*—1 to 3 mm long, pubescent, Brown N200B.

*Bloom period.*—June and July in Canby, Oreg.

Flower bud:

*Size.*—12 mm long and 5 mm wide at the widest point prior to opening.

*Description.*—Tubular.

*Surface texture.*—Pubescent.

*Color.*—Violet 85B.

Flower:

*Type.*—Zygomorphic.

*Shape.*—Bilabiate, tubular.

*Size.*—20 mm long and 6 mm wide.

*Corolla description.*—19 mm long and spreads to 11 mm wide; tube funnel form, 10 mm long and 2.5 mm to 5 mm wide; upper lobe hooded and notched, 6 mm long and 2 mm wide, obovate, tip obtuse, margin entire; three lower lobes, two smaller, spreading sideways and curling back, 2.5 mm long and 5 mm wide, acute, entire; the bottom lobe broad, reflexed, fan-shaped, cupped, 4 mm wide and 4 mm deep; tip truncate with fringe of small lobes, color inside and out Violet 85A except at tube where White 155A; inside glabrous and outside pubescent.

*Calyx description.*—10 mm long and 5 mm wide, pubescent outside and glabrous inside, 5 lobed, bilabiate, ovate, tip acute, margin entire, 3 upper lobes 3 mm long and 1.5 mm wide, 2 lower lobes 3 mm long and 2 mm wide, Red Purple 72B with longitudinal stripes of Green 147A.

*Pistil description.*—21 mm long, ovary 1 mm long, Yellow Green 151A, style 19 mm long, Violet 85D; stigma two-parted, 1 mm, Violet N88B.

*Stamen description.*—2 in number, included, 4 mm long and 1 mm wide, filaments Violet 85A; anthers 1.5 mm long and 1 mm wide, Yellow White 158D; pollen White NN155A.

*Fragrance.*—Strong foliage scent.

*Lastingness.*—A spike blooms for about 3 weeks on the plant.

Fruit/seed: 4 nutlets, 1 mm long, ovoid, Black 202A.

Pests and diseases: The new cultivar has no known resistances but has shown no problems in Canby, Oreg.

I claim:

1. A new and distinct form of *Salvia* plant substantially as shown and described.

* * * * *